(12) United States Patent
Lee et al.

(10) Patent No.: US 6,593,334 B1
(45) Date of Patent: Jul. 15, 2003

(54) CAMPTOTHECIN-TAXOID CONJUGATES AS ANTIMITOTIC AND ANTITUMOR AGENTS

(75) Inventors: Kuo-Hsiung Lee, Chapel Hill, NC (US); Hironari Ohtsu, Chapel Hill, NC (US); Yuka Nakanishi, Chapel Hill, NC (US); Kenneth F. Bastow, Chapel Hill, NC (US); Fang-Yu Lee, Taichung (TW)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/137,166

(22) Filed: May 2, 2002

(51) Int. Cl.[7] ................... A61K 49/22; C07D 31/4738
(52) U.S. Cl. ................. 514/283; 546/48; 435/184; 436/63; 436/64
(58) Field of Search .................. 514/283; 546/48; 435/184; 436/63, 64

(56) References Cited

U.S. PATENT DOCUMENTS

| 4,960,790 A | 10/1990 | Stella et al. |
| 5,459,269 A | 10/1995 | Comins |
| 6,063,923 A | 5/2000 | Fang et al. |
| 6,100,273 A | 8/2000 | Besterman et al. |
| 6,143,891 A | 11/2000 | Fang et al. |
| 6,331,635 B1 | 12/2001 | Bouchard et al. |
| 6,380,405 B1 | 4/2002 | Ekwuribe et al. |
| 6,420,377 B1 | 7/2002 | Lee et al. |

FOREIGN PATENT DOCUMENTS

| WO | WO 02/26220 | 4/2002 |

OTHER PUBLICATIONS

Murren, J.R. et al.: Dose escalation and pharmacokinetic study of irinotecan in combination with paclitaxel in patients with advanced cancer. Cancer Chemother. Pharmacol. vol. 46, pp. 43–50, 2000.*

* cited by examiner

Primary Examiner—Charanjit S. Aulakh
(74) Attorney, Agent, or Firm—Myers Bigel Sibley & Sajovec

(57) ABSTRACT

Compounds according to formula I: C'—L—T (I), wherein C' is a camptothecin group; L is a linking moiety; T is a taxoid group, pharmaceutically acceptable salt thereof. The compounds are useful in, among other things, treating cancer in subjects in need thereof, including cellular differentiation, and inhibiting cellular mitosis.

28 Claims, 4 Drawing Sheets

PACLITAXEL (1)

CAMPTOTHECIN (2)

3  L = PARA LINKAGE
4  L = ORTHO LINKAGE

CAMPTOTHECIN-TAXOID CONJUGATES AS ANTIMITOTIC AND ANTITUMOR AGENTS

STATEMENT OF FEDERAL SUPPORT

This invention was made with Government support under Grant No. CA17625 from the National Institute of Health. The government as certain rights in this invention.

FIELD OF THE INVENTION

The present invention relates to conjugates of camptothecin and analogs thereof and taxoid groups, pharmaceutical formulations containing the same, and methods of use thereof as antimitotic and antitumor agents, particularly for the treatment of cancers such as breast cancer, ovarian cancer and prostate cancer.

BACKGROUND OF THE INVENTION

Paclitaxel (1) as shown in FIG. 1 and camptothecin (2) also shown in FIG. 1 are both plant-derived antitumor agents currently in clinical use (M. C. Wani et al., *Taxus brevifolia*, 1971, 93, 2325–2327 and M. E. Wall et al., *J. Am. Chem. Soc.*, 1966, 88, 3888–3890). Paclitaxel was approved by the FDA for treatment of advanced ovarian cancer in 1992 and for treatment of breast cancer in 1994.

The mechanism of the antitumor effect of paclitaxel is antimitotic, specifically promoting the irreversible assembly of tubulin into microtubules (P. B. Schiff et al., *Nature*, 1979, 277, 665–667). Camptothecin also posseses significant antitumor activity which is attributable to inhibition of DNA topoisomerase I (DNA topo I) (Y. H. Hsiang et al., *J. Biol. Chem.*, 1985, 260, 14873–14878 and J. C. Wang, *Biochim. Biophys. Acta.*, 1987, 909, 1–9). Both compounds have been subject to continual structural modification aimed at developing more useful chemotherapeutic agents. However, although both paclitaxel and camptothecin possess potent antitumor activity, recent reports have shown that treatment with these drugs often results in a number of undesired side effects as well as multi-drug resistance. Therefore, it remains essential to develop new anticancer agents with fewer side effects and improved activity against various classes of tumors.

Previously we reported synthesis and evaluation of two 4'-O-demethyl epipodophyllotoxin-camptothecin conjugates (3 and 4 as shown in FIG. 1) as inhibitors of mammalian DNA topoisomerases I and II (K. F. Bastow et al., *Bioorg. Med. Chem.*, 1997, 5, 1481–1488). The most active conjugate inhibited cell growth similarly to both topo I- and II-inhibitory components. These conjugates were more cytotoxic than epipodophyllotoxin in several cancer cell lines including HOP-62 leukemia, SW-620 colon cancer, MCF/ADR adriamycin-resistant breast cancer and A-498 renal cancer. One conjugate was more active than either etoposide or (2) against human KB (nasopharnyx) and DU-145 (prostate) tumor cell growth in nude mice. Currently, there are several reports describing conjugates between paclitaxel and either daunorubicin or chlorambucil (A. K. Kar et al., *Bioorg. Med. Chem. Let.*, 2000, 10, 261–264 and M. D. Wittman et al., *Bioorg. Med. Chem. Let.*, 2001, 11, 811–814). However, DNA topisomerase inhibitor-paclitaxel hybrids have not been investigated.

SUMMARY OF THE INVENTION

According to embodiments of the present invention, the present invention relates to a compound according to formula I:

wherein:
C' is a camptothecin group of formula II:

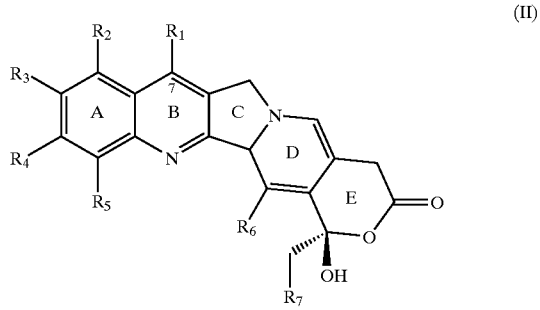

wherein:
$R_1$ is selected from the group consisting of H, alkyl, aldehyde, carbonyl, alkoxy, alkylaryl, hydroxyalkyl, haloalkyl, aminoalkyl, dialkylamino, dialkylaminoalkyl, cycloaminoalkyl, aryl, aryloxy, C-glycal, nitro, cyano and O-glycosyl;

$R_2$, $R_3$, $R_4$ and $R_5$ are each independently selected from the group consisting of H, amino, hydroxy, alkyl, alkoxy, alkylthiol, alkylamino, aminoalkyl, di(alkyl)amino, cycloaminoalkyl, aminoalkoxy, aryl, aryloxy, C-glycal, cyano, methylenedioxy, formyl, nitro, halo, azido, amido, hydrazino, any of the twenty standard amino acids bonded to the A ring via the amino-nitogen atom, $SR_8$, $NR_8R_8$, or O-glycosyl; or $R_3$ and $R_4$ together form a 5- or 6-member aromatic or dioxolane ring; and wherein $R_2$ and $R_3$, $R_3$ and $R_4$, or $R_4$ and $R_5$ taken together;

Subject to the proviso that one of $R_1$, $R_2$, $R_3$, $R_4$ and $R_5$ is a covalent bond to L;

$R_6$ is H, halo, alkyl, alkoxy, alkylaryl, hydroxyalkyl, or haloalkyl;

$R_7$ is alkyl, alkylaryl, hydroxyalkyl, or aryl;

$R_8$ is independently selected from the group consisting of H, alkyl, alkylaryl, hydroxyalkyl, aminoalkyl, acyl, or aryl;

L is a linking moiety;
T is a taxoid group, of formula III:

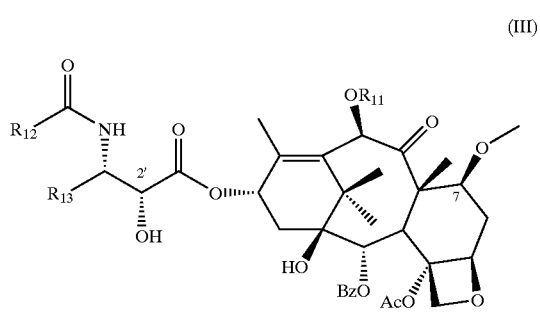

wherein
$R_{11}$ is selected from the group consisting of H, alkyl, alkoxy, aminoalkyl and acyl;

R$_{12}$ and R$_{13}$ are each independently selected from the group consisting of H, alkyl, aryl, alkoxy, alkylaryl, hydroxyalkyl, haloalkyl, aminoalkyl, dialkylamino, dialkylaminoalkyl, cycloaminoalkyl, aryloxy, nitro, cyano, and halo; or a pharmaceutically acceptable salt thereof.

According to other embodiments of the present invention, the present invention relates to a pharmaceutical formulation comprising a compound according to Formula I above in a pharmaceutically acceptable carrier.

According to still other embodiments of the present invention, the present invention relates to a method of treating cancer, comprising administering to a subject in need thereof a treatment effective amount of a compound according to Formula I above. Examples of cancers that may be treated include, but are not limited to, small cell lung cancer, testicular cancer, lymphoma, leukemia, esophageal cancer, stomach cancer, colon cancer, breast cancer, ovarian cancer, central nervous system cancer, liver cancer and prostate cancer.

According to yet other embodiments of the present invention, the present invention relates to a method of inducing cellular differentiation, the method comprising contacting (in vivo or in vitro) a cancer cell with a differentiation effective amount of a compound according to formula I above.

According to other embodiments of the present invention, the present invention relates to a method of inhibiting cellular mitosis, the method comprising contacting (in vivo or in vitro) a cell with a mitosis inhibiting amount of a compound according to formula I above.

DETAILED DESCRIPTION OF THE INVENTION

Figure 1:
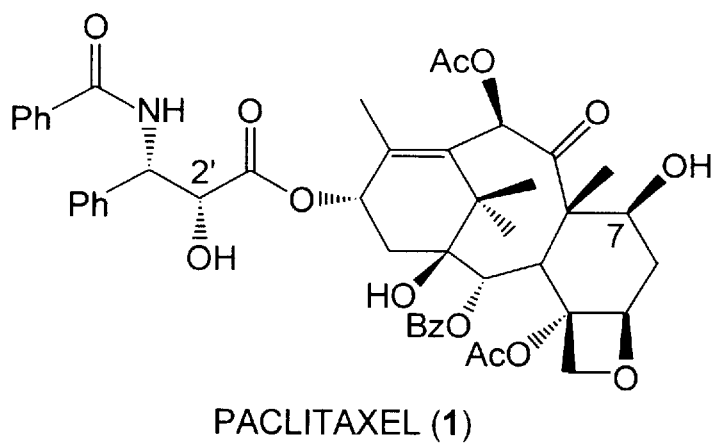
FIG. 1 illustrates the structures of various precursor compounds related to the present invention.
Figure 1:
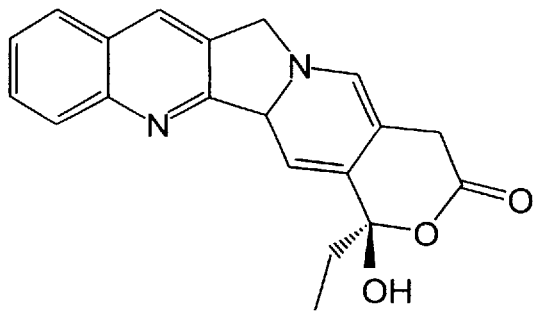
Figure 1:
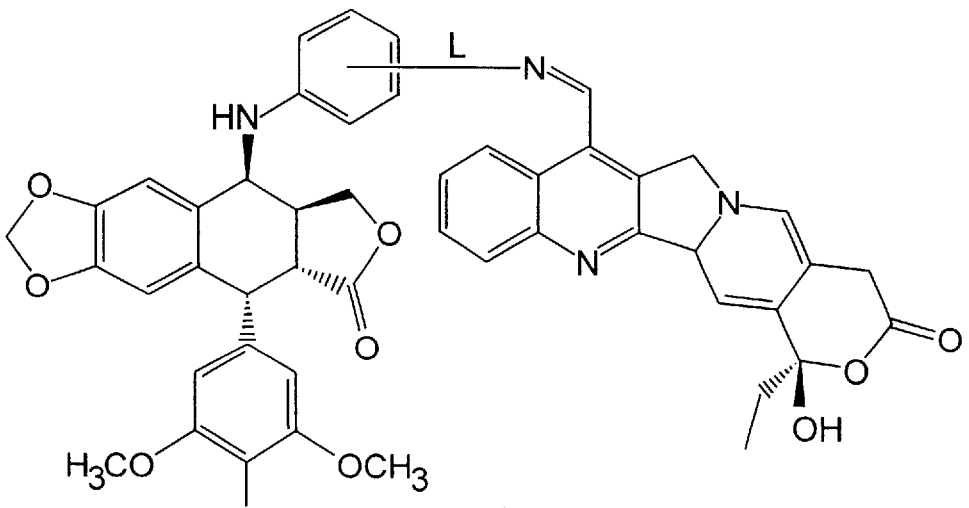

The present invention will now be described more fully hereinafter with reference to the accompanying figures, which further illustrate the invention described herein. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

The term "alkyl" or "loweralkyl" as used herein refers to C1 to C4, C6 or C8 alkyl, which may be linear or branched and saturated or unsaturated.

"Cycloalkyl" is specified as such herein, and is typically C3, C4 or C5 to C6 or C8 cycloalkyl.

"Alkenyl" or "loweralkenyl" as used herein likewise refers to C1 to C4 alkenyl, and alkoxy or loweralkoxy as used herein likewise refers to C1 to C4 alkoxy.

"Alkoxy" as used herein refers to linear or branched, saturated or unsaturated oxo-hydrocarbon chains, including for example methoxy, ethoxy, propoxy, isopropoxy, butoxy, and t-butoxy.

The term "aryl" as used herein refers to C3 to C10 cyclic aromatic groups such as phenyl, naphthyl, and the like, and includes substituted aryl groups such as tolyl.

"Halo" as used herein refers to any halogen group, such as chloro, fluoro, bromo, or iodo.

The term "hydroxyalkyl" as used herein refers to C1 to C4 linear or branched hydroxy-substituted alkyl, i.e., —CH$_2$OH, —(CH$_2$)$_2$OH, etc.

The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc.

The term "oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

The present invention is concerned primarily with the treatment of human subjects, but may also be employed for the treatment of other animal subjects (i.e., mammals, avians) for veterinary purposes. Mammals are preferred, with humans being particularly preferred.

In general, active compounds of the present invention have a structure according to formula I:

$$C'—L—T \qquad (I)$$

wherein C' is a camptothecin group including camptothecin and analogs thereof, T is a taxoid group, and L is a covalent linking group. Active compounds as used herein include the pharmaceutically acceptable salts thereof. The invention includes the respective dextrorotatory or levorotatory pure preparations, as well as mixtures (racemic or enantiomerically enriched mixtures) thereof. The various groups that can be used in conjunction with formula I above are discussed in greater detail below.

A. Camptothecin

Any camptothecin or camptothecin analog may be used to carry out the present invention. Camptothecin is known and can be produced in accordance with known techniques. See generally Merck Index, Monograph No. 1783. (12th ed. 1996).

Examples of camptothecin analogs that can be used to carry out the present invention include, but are not limited to, those described in U.S. Pat. No. 4,894,456 to Wall et al.; U.S. Pat. No. 4,399,282 to Miyasaka, et al.; U.S. Pat. No. 4,399,276 to Miyasaka, et al.; U.S. Pat. No. 4,943,579 to Vishnuvajjala, et al.; European Patent Application 0 321 122 A2; U.S. Pat. No. 4,473,692 Miyasaka, et al. European Patent application No. 0 325 247 A2; European Patent application 0 556 585 A2 filed by Takeda Chemical Industries; U.S. Pat. No. 4,981,968 to Wall, et al.; U.S. Pat. No. 5,049,668 to Wall, et al.; U.S. Pat. No. 5,162,532 to Comins, et al.; U.S. Pat. No. 5,180,722 to Wall, et al; U.S. Pat. No. 5,200,524 to Comins, et al.; U.S. Pat. No. 5,459,269 to Comins, et al.; U.S. Pat. No. 5,162,532 to Fang et al.; and U.S. Pat. No. 6,328,953 to Angelucci et al. (the disclosures of all patent references cited herein are incorporated by reference in their entirety). Such compounds are generally of formula II:

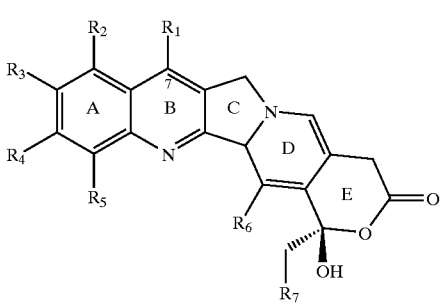

(II)

wherein:

$R_1$ is selected from the group consisting of H, alkyl, aldehyde, carbonyl, alkoxy, alkylaryl, hydroxyalkyl, haloalkyl, aminoalkyl, dialkylamino, dialkylaminoalkyl, cycloaminoalkyl, aryl, aryloxy, C-glycal, nitro, cyano and O-glycosyl;

$R_2$, $R_3$, $R_4$ and $R_5$ are each independently selected from the group consisting of H, amino, hydroxy, alkyl, alkoxy, alkylthiol, alkylamino, aminoalkyl, di(alkyl) amino, cycloaminoalkyl, aminoalkoxy, aryl, aryloxy, C-glycal, cyano, methylenedioxy, formyl, nitro, halo, azido, amido, hydrazino, any of the twenty standard amino acids bonded to the A ring via the amino-nitogen atom, $SR_8$, $NR_8R_8$, or O-glycosyl; or $R_3$ and $R_4$ together form a 5- or 6-member aromatic or dioxolane ring; and wherein $R_2$ and $R_3$, $R_3$ and $R_4$, or $R_4$ and $R_5$ taken together;

Subject to the proviso that one of $R_1$, $R_2$, $R_3$, $R_4$ and $R_5$ is a covalent bond to L;

$R_6$ is H, halo, alkyl, alkoxy, alkylaryl, hydroxyalkyl, or haloalkyl;

$R_7$ is alkyl, alkylaryl, hydroxyalkyl, or aryl;

$R_8$ is independently selected from the group consisting of H, alkyl, alkylaryl, hydroxyalkyl, aminoalkyl, acyl, or aryl.

B. Taxoid Group

Any taxoid group may be used to carry out the present invention. Taxoid groups are known and can be produced in accordance with known techniques. See generally Merck Index, Monograph No. 1783. (12th ed. 1996).

Preferred taxanes are those having the constituents known in the art to be required for enhancement of microtubule formation, e.g., paclitaxel and docetaxel. The structures of paclitaxel and docetaxel are known in the art. Examples of taxoid groups that can be used to carry out the present invention include, but are not limited to, those described in U.S. Pat. Nos. 5,614,645 to Kingston et al.; U.S. Pat. No. 6,028,206 to Chattopadhyay et al; U.S. Pat. No. 5,411,984 to Kingston et al.; and U.S. Pat. No. 5,508,447 to Magnus (the disclosures of all patent references cited herein are incorporated by reference in their entirety). A taxoid group that can be used to carry out the presentation is represented by formula III:

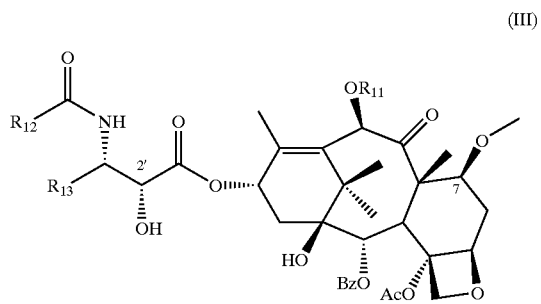

(III)

wherein:

$R_{11}$ is selected from the group consisting of H, alkyl, alkoxy, aminoalkyl and acyl;

$R_{12}$ and $R_{13}$ are each independently selected from the group consisting of H, alkyl, aryl, alkoxy, alkylaryl, hydroxyalkyl, haloalkyl, aminoalkyl, dialkylamino, dialkylaminoalkyl, cycloaminoalkyl, aryloxy, nitro, cyano, and halo;

or a pharmaceutically acceptable salt thereof.

C. Linking Moiety

Linking groups that may be used to form covalent conjugates of two functional moieties are known in the art. The specific linking group employed will depend upon the particular synthetic method used to make the covalent conjugate, as will be appreciated by those skilled in the art. A suitable linking group will permit the joining of camptothecin (C') and taxoid (T) groups to provide a metabolically stable conjugate (i.e., a conjugate for which steric hinderance will not be so strong as to prevent the joining of the C' and T groups).

In general, the linking moiety may comprise an aliphatic, aromatic, or mixed aliphatic and aromatic group (e.g., alkyl, aryl, alkylaryl, etc.) and contain one or more amino acids or hetero atoms such as N, O, S, etc. For example, the linking group L may be a compound of the formula —$L_a$—$L_b$—, where $L_b$ is present or absent and $L_a$ and $L_b$ are each independently selected from the group consisting of:

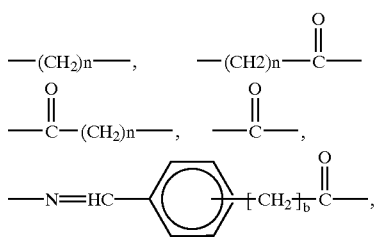

-continued

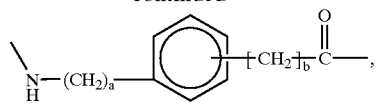

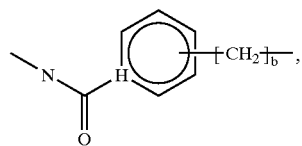

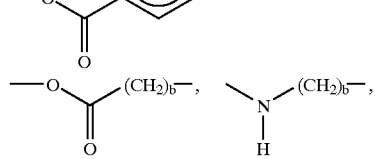

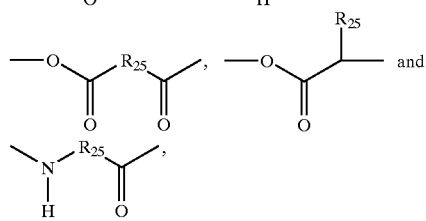

wherein:
n is 0 to 6, a is 0 to 3 and b is 0 to 3; and $R_{25}$ is selected from the group consisting of alkylene, alkenyl, and arylenyl.

The linking group may also comprise a linking moiety at position 7 of the taxoid group and at $R_1$ of the camptothecin group of the formula IV:

$$—X—R_{21}—A—\qquad(IV)$$

wherein:
X is an electron withdrawing group; and
$R_{21}$ is selected from the group consisting of alkylene and arylalkylene;
A is selected from the group consisting of amino and imine.

The linking group may also comprise a linking moiety comprising the formula V:

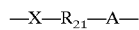
(V)

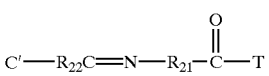

wherein:
$R_{21}$ is selected from the group consisting of alkylene and arylalkylene;
$R_{22}$ is selected from the group consisting of H and alkyl.

D. Specific Compounds

Specific compounds within the scope of the present invention include, but are not limited to:

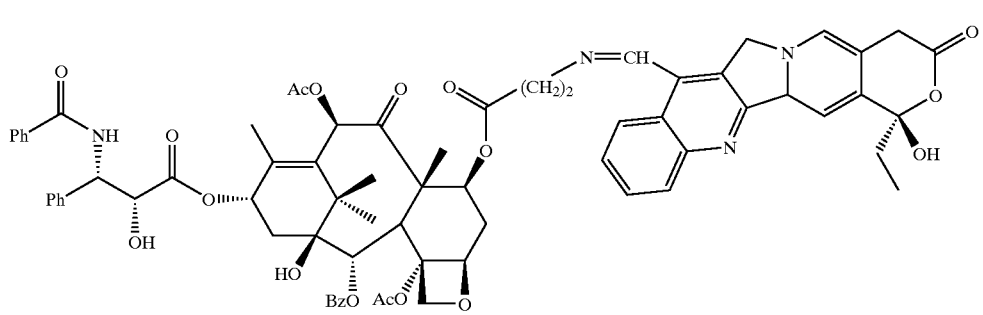
(16)

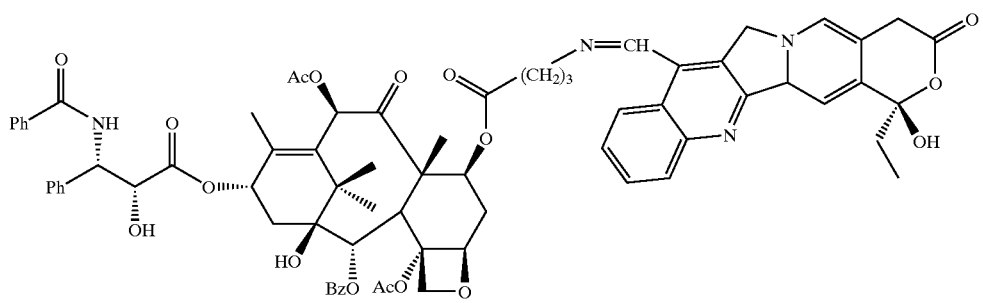
(17)

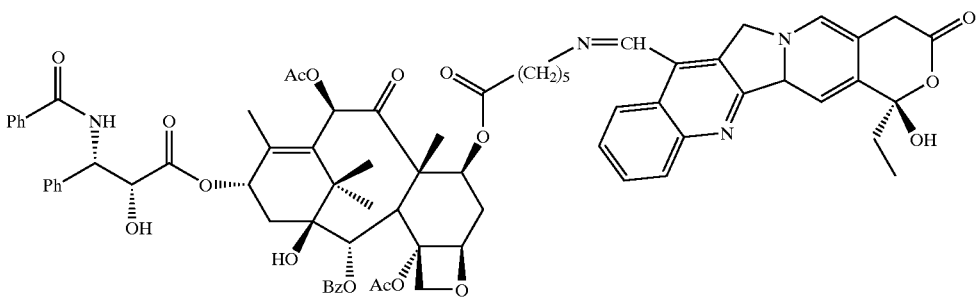

(18)

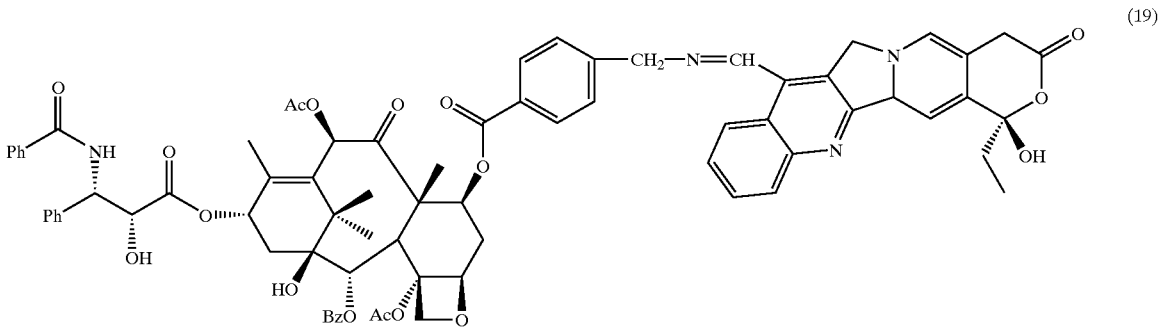

(19)

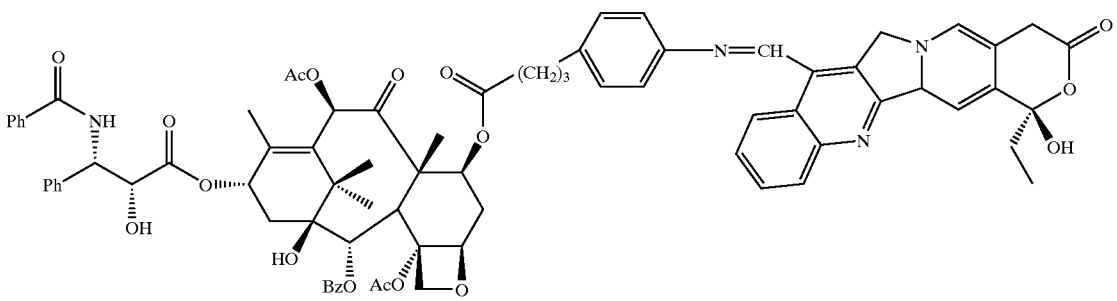

(20)

E. Synthesis of Compounds

Synthesis of compounds of the present invention may be determined by the particular linking chemistry employed. Variations on the following general synthetic method will be readily apparent to those skilled in the art and are deemed to be within the scope of the present invention. In general, the conjugates of formula I may be prepared by refluxing camptothecin compounds with taxoid compounds in benzene.

As a specific example, the conjugates 16 through 20 above may be prepared by dissolving 7-formyl camptothecin and taxoid in dry benzene. The solution is then refluxed over 4 Å molecular sieves overnight. The mixture is filtered and evaporated in vacuo to give crude paclitaxel-camptothecin conjugates. The product is purified by Sephadex LH-20 column chromatography with $CHCl_3$—MeOH (1:1) as eluent.

F. Pharmaceutically Acceptable Salts

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

G. Pharmaceutical Formulations

The camptothecin and taxoid compounds of formula I of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of formula I may be formulated for administration for the treatment of a variety of conditions. In the manufacture of a pharmaceutical formulation according to the invention, the compounds of formula I and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such Formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis\tris buffer (pH 6) or ethanol/water and contain from 0.01 to 0.2 M active ingredient.

H. Methods of Use

In addition to the compounds of formula I, the present invention also provides useful therapeutic methods. For example, the present invention provides a method of inducing antitumor activity. More specifically, the present invention provides a method of inhibiting DNA topoisomerase I. The method includes contacting topoisomerase I in vitro or in vivo with an inhibitory effective amount of a compound of formula I. The inhibition of topoisomerase I is a useful means of inhibiting tumor or cancer cell growth.

The present invention also provides a method of inducing cellular differentiation. The method includes contacting a cancer cell with a differentiation effective amount of a compound of formula I. Cancer cells which may be differentiated include cells from small cell lung cancer, testicular cancer, lymphoma, leukemia, esophageal cancer, stomach cancer, colon cancer, breast cancer, ovarian cancer, central nervous system cancer, liver cancer and prostate cancer.

The present invention also provides a method of treating cancer in a subject afflicted with cancer. The method includes administering to the subject in an effective cancer treating amount a compound of formula I. The methods are useful for the treatment of a variety of cancer cells which include but are not limited to small cell lung cancer, testicular cancer, lymphoma, leukemia, esophageal cancer, stomach cancer, colon cancer, breast cancer, ovarian cancer, central nervous system cancer, liver cancer and prostate cancer.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of formula I, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples.

EXAMPLES

A. Materials and Methods

Paclitaxel (1) was obtained from Yung Shin Pharmaceutical Ind. Co., Ltd., Taiwan. Preparation of 7-formylcamptothecin (5) (shown in FIG. 1) from (2) was performed as reported by Bastow et al. (1997) *Bioorg. Med. Chem.* 5: 1481. All reagents and solvents were reagent grade or were purified by standard methods before use. $^1$H NMR spectra were obtained on a Varian Gemini-300 spectrometer using TMS as the internal standard. Chemical shifts (δ values) and coupling constants (J values) are given in ppm and Hz, respectively. Optical rotations were measured with a JASCO DIP-1000 digital polarimeter. Column chromatography was carried out on silica gel 60 (Merck 230–400 mesh), and thin layer chromatography (TLC) was performed using pre-coated silica gel on aluminum plates (Aldrich, Inc.). Elemental analyses were performed by Atlantic Microlab Inc., Norcross, Ga. N-Cbz-animo acids were prepared from the appropriate amino acids using standard methodology as described in Berger et al. (1954) *J. Am. Chem. Soc.* 76:5552 using benzylchloroformate, except for N-Cbz-β-alanine (Sigma). 2'-O-Cbz-paclitaxel was synthesized as described by Guy et al. (1996) *Chem. Biol.* 3:1021.

General Procedure for 7-O-Acylation of 2'-O-Cbz-paclitaxel. A solution of 2'-O-Cbz-paclitaxel and 4-(N,N-dimethylamino)pyridine (1.0 equiv.) in dry dichloromethane (5 mL) under nitrogen was treated with the appropriate N-Cbz-amino acid (5.0 equiv.) and dicyclohexylcarbodiimide (DCC, 5.0 equiv.) overnight at room temperature. The mixture was diluted with dichloromethane (5 mL) and filtered to remove the urea precipitate. The solvent was evaporated in vacuo and the resulting residue was purified by silica gel column chromatography using an n-hexane-EtOAc solvent system (2:1 to 1:1) to afford the desired 2'-O-Cbz-7-O-acyl paclitaxel as the sole product.

2'-O-Cbz-7-(N-Cbz-β-alanyl)-paclitaxel (6). Yield 90.5% (starting with 59.3 mg of 2'-O-Cbz-paclitaxel); white powder, $[\alpha]_D$–44.7° (c 0.76, CHCl$_3$); $^1$H NMR (CDCl$_3$): δ 1.16 (3H, s), 1.22 (3H, s), 1.81 (3H, s), 2.00 (3H, s), 2.06 (3H, s), 2.46 (3H, s), 3.46 (2H, m), 3.96 (1H, d, J=7.0 Hz), 4.20 (1H, d, J=8.5 Hz), 4.33 (1H, d, J=8.5 Hz), 4.95 (1H, d, J=8.5 Hz), 5.11 (2H, m), 5.17 (2H, m), 5.46 (1H, d. J=2.5 Hz), 5.64 (1H, dd, J=7.2, 9.8 Hz), 5.70 (1H, d, J=7.0 Hz), 5.77 (1H, t, J=5.1 Hz), 5.98 (1H, d, J=9.0 Hz), 6.26 (1H, t, J=9.3 Hz), 6.29 (1H, s), 6.94 (1H, d, J=9.0 Hz), 7.30–7.42 (band, 17H), 7.44–7.54 (3H, m), 7.62 (1H, m), 7.74 (2H, d, J=8.5 Hz), 8.13 (2H, d, J=8.5 Hz); FAB-MS m/z 1193 [M+1]$^+$. All data are in agreement with previously reported literature values.

2'-O-Cbz-7-(N-Cbz-4-aminobutyroyl)-paclitaxel (7). Yield 97.2% (starting with 69.1 mg of 2'-O-Cbz-paclitaxel); white powder, $[\alpha]_D$–31.5° (c 0.46, CHCl$_3$); $^1$H NMR (CDCl$_3$): δ 1.16 (3H, s), 1.21 (3H, s), 1.81 (3H, s), 1.99 (3H, s), 2.09 (3H, s), 2.45 (3H, s), 3.19–3.40 (2H, m), 3.94 (1H, d, J=6.9 Hz), 4.20 (1H, d, J=8.5 Hz), 4.33 (1H, d, J=8.5 Hz), 4.95 (1H, d, J=8.5 Hz), 5.08 (2H, s), 5.17 (2H, m), 5.45 (1H, d, J=2.4 Hz), 5.57 (1H, dd, J=6.9, 10.2 Hz), 5.71 (1H, d, J=6.9 Hz), 5.73 (1H, t, J=5.1 Hz), 5.98 (1H, dd, J=2.4, 9.0 Hz), 6.24 (1H, s), 6.26 (1H, t, J=9.3 Hz), 6.92 (1H, d, J=9.0 Hz), 7.27–7.46 (band, 16H), 7.48–7.54 (3H, m), 7.62 (1H, m), 7.73 (2H, d, J=8.5 Hz), 8.13 (2H, d, J=8.5 Hz); ESI-MS m/z 1230 [M+Na]$^+$.

2'-O-Cbz-7-(N-Cbz-6-aminohexanoyl)-paclitaxel (8). Yield 94.7% (starting with 78.3 mg of 2'-O-Cbz-paclitaxel); white powder, $[\alpha]_D$–44.0° (c 1.04, CHCl$_3$); $^1$H NMR (CDCl$_3$): δ 1.16 (3H, s), 1.21 (3H, s), 1.81 (3H, s), 2.00 (3H, s), 2.13 (3H, s), 2.45 (3H, s), 3.19 (2H, dd, J=6.3, 12.9 Hz), 3.96 (1H, d, J=6.6 Hz), 4.19 (1H, d, J=8.5 Hz), 4.32 (1H, d, J=8.5 Hz), 4.96 (1H, d, J=8.7 Hz), 5.08 (2H, s), 5.16 (2H, m), 5.45 (1H, d, J=2.4 Hz), 5.60 (1H, dd, J=7.2, 10.5 Hz), 5.71 (1H, d, J=6.9 Hz), 5.98 (1H, dd, J=3.0, 9.5 Hz), 6.26 (1H, t, J=9.0 Hz), 6.28 (1H, s), 6.95 (1H, d, J=9.3 Hz), 7.26–7.43 (band, 16H), 7.46–7.53 (3H, m), 7.61 (1H, m), 7.73 (2H, d, J=8.5 Hz), 8.13 (2H, d, J=8.5 Hz); FAB-MS m/z 1236 [M+1]$^+$.

2'-O-Cbz-7-(N-Cbz-4-methylaminobenzoyl)-paclitaxel (9). Yield 89.1% (starting with 70.4 mg of 2'-O-Cbz-paclitaxel); white powder, $[\alpha]_D$–28.2° (c 0.99, CHCl$_3$); $^1$H NMR (CDCl$_3$): δ 1.19 (3H, s), 1.21 (3H, s), 1.95 (3H, s), 1.97 (3H, s), 2.04 (3H, s), 2.48 (3H, s), 4.05 (1H, d, J=6.9 Hz), 4.24 (1H, d, J=8.5 Hz), 4.37 (1H, d, J=8.5 Hz), 4.42 (1H, d, J=6.0 Hz), 5.01 (1H, d, J=8.4 Hz), 5.10–5.22 (6H, m), 5.48 (1H, d, J=2.7 Hz), 5.74–5.81 (2H, m), 5.99 (1H, dd, J=2.7, 9.2 Hz), 6.27 (1H, t, J=9.0 Hz), 6.41 (1H, s), 6.97 (1H, d, J=9.3 Hz), 7.29–7.42 (band, 19H), 7.46–7.54 (3H, m), 7.62 (1H, m), 7.74 (2H, d, J=8.5 Hz), 7.89 (2H, d, J=8.4 Hz). 8.15 (2H, d, J=8.5 Hz); ESI-MS m/z 1277 [M+Na]$^+$.

2'-O-Cbz-7-(N-Cbz-4-(4-aminophenyl)-butyroyl)-paclitaxel (10). Yield 83.8% (starting with 66.8 mg of 2'-O-Cbz-paclitaxel); white powder, $[\alpha]_D$–46.5° (c 0.40, CHCl$_3$); $^1$H NMR (CDCl$_3$): δ 1.17 (3H, s), 1.21 (3H, s), 1.81 (3H, s), 2.01 (3H, s), 2.13 (3H, s), 2.45 (3H, s), 3.96 (1H, d, J=6.9 Hz), 4.19 (1H, d, J=8.5 Hz), 4.33 (1H, d, J=8.5 Hz), 4.96 (1H, d, J=8.1 Hz), 5.12–5.21 (4H, m), 5.46 (1H, d, J=2.7 Hz), 5.60 (1H, dd, J=7.2, 10.5 Hz), 5.70 (1H, d, J=7.2 Hz), 5.98 (1H, dd, J=2.7, 9.2 Hz), 6.26 (1H, t, J=9.0 Hz), 6.29 (1H, s), 6.66 (1H, s), 6.94 (1H, d, J=9.3 Hz), 7.12 (2H, d, J=8.7 Hz), 7.26–7.42 (band, 19H), 7.46–7.53 (3H, m), 7.61 (1H, m), 7.73 (2H, d, J=8.5 Hz), 8.13 (2H, d, J=8.5 Hz); FAB-MS m/z 1306 [M+Na]$^+$.

Figure 2:
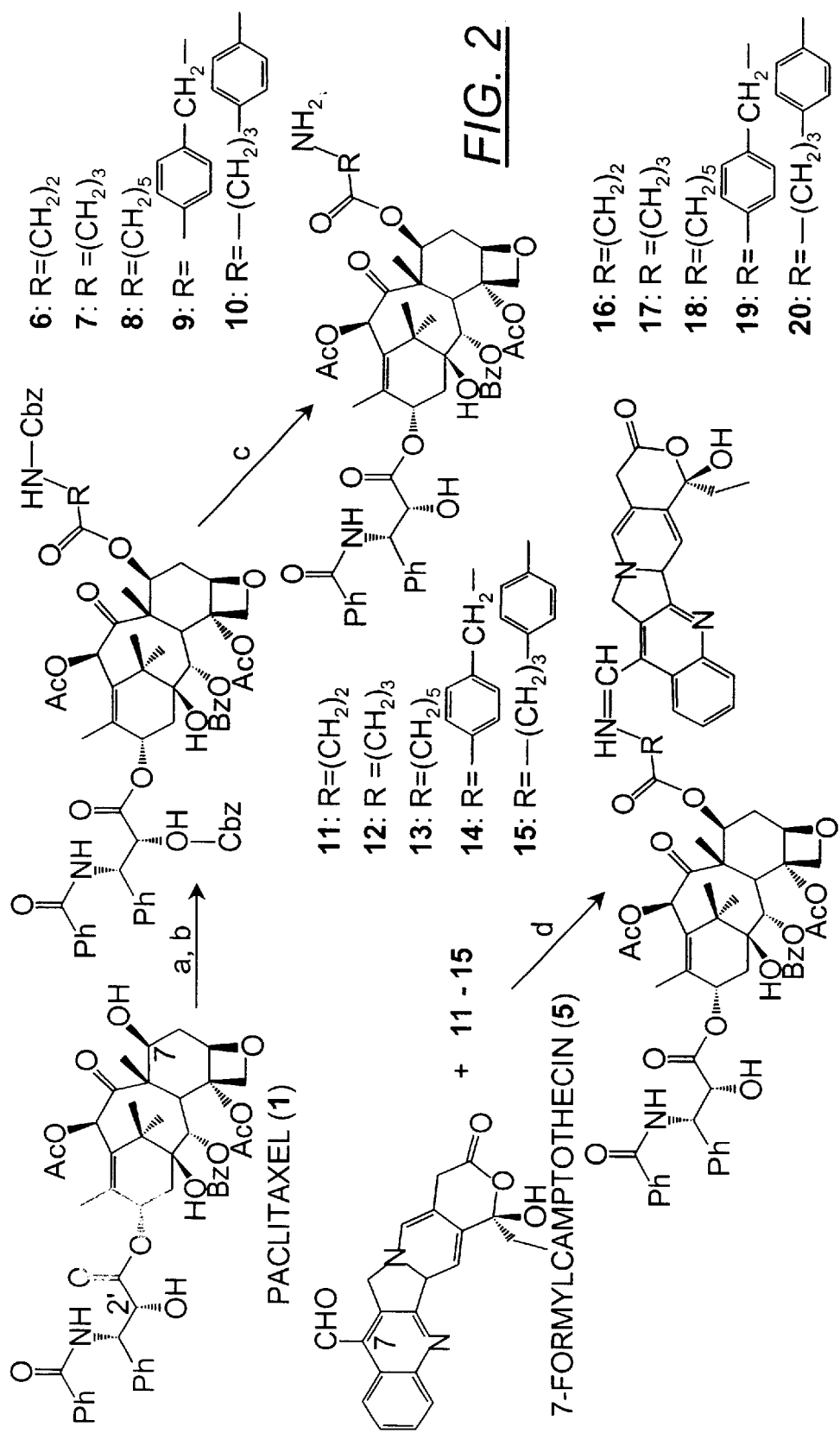
FIG. 2 illustrates embodiments of a synthesis route for preparation of compounds of the present invention.

General Procedure for Removal of the Benzyloxycarbonyl (Cbz) protecting group. A solution of taxoid (6–10 as shown in FIG. 2) in methanol under nitrogen was treated with 50 wt % of 5% palladium on activated carbon (Degussa type E101 NO/W) and placed under hydrogen (40 psi). The mixture was shaken in a Parr apparatus for 7 h then the content was filtered to remove the catalyst and evaporated to dryness in vacuo to give the desired deprotected compounds 11–15 (as shown in FIG. 2).

7-O-β-Alanylpaclitaxel (11). Yield 81.2% (starting with 47.2 mg of 6); white film, $[\alpha]_D$–39.1° (c 0.34, MeOH); $^1$H NMR (CD$_3$OD): δ 1.10 (3H, s), 1.16 (3H, s), 1.78 (3H, s), 1.88 (3H, s), 2.16 (3H, s), 2.37 (3H, s), 3.12–3.22 (2H, m), 3.90 (1H, d, J=7.0 Hz), 4.20 (2H, dd, J=7.0, 14.0 Hz), 4.73 (1H, d, J=6.0 Hz), 5.00 (1H, m), 5.64 (3H, m), 6.15 (1H, br t, J=6.2 Hz), 6.23 (1H, s), 7.28–7.68 (band, 11H), 7.85 (2H, d, J=8.5 Hz), 8.10 (2H, d, J=8.5 Hz); FAB-MS m/z 925 [M+1]$^+$. All data are in agreement with reported literature values.

7-O-(4-Aminobutyroyl)paclitaxel (12). Yield 92.7% (starting with 59.1 mg of 7); white film, $[\alpha]_D$ −29.7° (c 0.37, MeOH); $^1$H NMR (CD$_3$OD): δ 1.11 (3H, s), 1.16 (3H, s), 1.78 (3H, s), 1.87 (3H, s), 2.16 (3H, s), 2.37 (3H, s), 3.01 (2H, t, J=7.5 Hz), 3.90 (1H, d, J=6.9 Hz), 4.20 (2H, br t, J=8.7 Hz), 4.75 (1H, d, J=5.4 Hz), 5.00 (1H, d, J=9.3 Hz), 5.59–5.66 (3H, m), 6.15 (1H, br t, J=6.2 Hz), 6.21 (1H, s), 7.26–7.69 (band, 11H), 7.85 (2H, d, J=8.5 Hz), 8.10 (2H, d, J=8.5 Hz); ESI-MS m/z 939 [M+1]$^+$.

7-O-(6-Aminohexanoyl)paclitaxel (13). Yield 81.1% (starting with 67.1 mg of 8); white film, $[\alpha]_D$ −26.0° (c 0.53, MeOH); $^1$H NMR (CD$_3$OD): δ 1.11 (3H, s), 1.16 (3H, s), 1.77 (3H, s), 1.88 (3H, s), 2.14 (3H, s), 2.37 (3H, s), 2.92 (2H, m), 3.90 (1H, d, J=6.9 Hz), 4.20 (2H, m), 4.75 (1H, d, J=5.4 Hz), 4.99 (1H, d, J=9.0 Hz), 5.58 (1H, dd, J=7.8, 10.5 Hz), 5.60–5.70 (2H, m), 6.15 (1H, br t, J=6.2 Hz), 6.24 (1H, s), 7.26–7.72 (band, 11H), 7.85 (2H, d, J=8.5 Hz), 8.10 (2H, d, J=8.5 Hz); FAB-MS m/z 968 [M+1]$^+$.

7-O-(4-Methylaminobenzoyl)paclitaxel (14). Yield 96.7% (starting with 58.1 mg of 9); white film, $[\alpha]_D$ −12.9° (c 0.38, MeOH); $^1$H NMR (CD$_3$OD): δ 1.13 (3H, s), 1.15 (3H, s), 1.91 (9H, s), 2.40 (3H, s), 3.90 (1H, d, J=6.9 Hz), 4.18–4.30 (4H, m), 4.76 (1H, d, J=5.7 Hz), 5.05 (1H, m), 5.65 (1H, d, J=5.1 Hz), 5.70 (1H, d, J=7.2 Hz), 5.76 (1H, dd, J=7.2, 10.5 Hz), 6.16 (1H, br t, J=6.2 Hz), 6.35 (1H, s), 7.28–7.71 (band, 13H), 7.85 (2H, d, J=8.5 Hz), 7.94 (2H, d, J=8.5 Hz), 8.12 (2H, d, J=8.5 Hz); ESI-MS m/z 1009 [M+Na]$^+$.

7-O-(4-(4-Aminophenyl)butyroyl)paclitaxel (15). Yield 81.3% (starting with 67.1 mg of 10); white film, $[\alpha]_D$ −45.3° (c 0.15, MeOH); $^1$H NMR (CD$_3$OD): δ 1.11 (3H, s), 1.14 (3H, s), 1.77 (3H, s), 1.89 (3H, s), 2.09 (3H, s), 2.36 (3H, s), 2.46 (2H, t, J=5.7 Hz), 3.89 (1H, d, J=6.9 Hz), 4.19 (2H, brs), 4.75 (1H, d, J=5.4 Hz), 4.97 (1H, d, J=9.6 Hz), 5.56 (1H, dd, J=7.8, 10.5 Hz), 5.63–5.66 (2H, m), 6.15 (1H, br t, J=6.2 Hz), 6.26 (1H, s), 6.67 (2H, d, J=8.4 Hz), 6.93 (2H, d, J=8.4 Hz), 7.28 (1H, m), 7.38–7.68 (band, 10H), 7.84 (2H, d, J=8.5 Hz), 8.10 (2H, d, J=8.5 Hz); FAB-MS m/z 1038 [M+Na]$^+$.

General Procedure for the Synthesis of Paclitaxel-Camptothecin Conjugates (16–20). A solution of taxoid (11–15) and 7-formylcamptothecin (1.2 equiv.) in dry benzene (10 mL) was refluxed over 4 Å molecular sieves overnight. The mixture was filtered and evaporated in vacuo to give crude paclitaxel-camptothecin conjugates (16–20 as shown in FIG. 2). The product was purified by Sephadex LH-20 column chromatography with CHCl$_3$—MeOH (1:1) as eluent. Elemental analysis data for conjugates 16–20 are shown in Table 1 below.

Conjugate 16: Yield 85.4% [starting with 14.2 mg (0.015 mmol) of 11]; pale yellow amorphous solid, $[\alpha]_D$ −33.9° (c 0.18, CHCl$_3$), $^1$H NMR (CDCl$_3$): δ 1.02 (3H, t, J=7.5 Hz), 1.18 (3H, s), 1.25 (3H, s), 1.80 (3H, s), 1.85 (3H, s), 2.19 (3H, s), 2.37 (3H, s), 3.92 (1H, d, J=6.6 Hz), 4.14 and 4.29 (each 1H, d, J=8.4 Hz), 4.80 (1H, brs), 4.90 (1H, d, J=9.3 Hz), 5.21 (1H, d, J=16.5 Hz), 5.40 (2H, s), 5.58–5.70 (3H, m), 5.80 (1H, dd, J=8.9, 2.1 Hz), 6.19 (1H, t, J=9.0 Hz), 6.24 (1H, s), 7.27–7.86 (16H, m), 8.09 (2H, d, J=7.2 Hz), 8.27 (1H, d, J=8.4 Hz), 8.45 (1H, d, J=8.4 Hz), 9.32 (1H, s); FAB-MS m/z (rel. int.) 1284 [M+1]$^+$ (35), 1224 (15), 940 (51), 449 (77), 289 (98), 240 (100). Anal. (C$_{71}$H$_{72}$N$_4$O$_{18}$): Theory: C, 67.18; H, 5.72. Found C, 67.12; H, 5.69.

Conjugate 17: Yield 60.7% [starting with 27.0 mg (0.029 mmol) of 12]; pale yellow amorphous solid, $[\alpha]_D$ −17.2° (c 0.47, CHCl$_3$), $^1$H NMR (CDCl$_3$): δ 1.04 (3H, t, J=7.5 Hz), 1.16 (3H, s), 1.20 (3H, s), 1.81 (3H, s), 1.83 (3H, s), 2.04 (3H, s), 2.38 (3H, s), 3.81–3.93 (4H, m), 4.18 and 4.31 (each 1H, d, J=8.4 Hz), 4.81 (1H, dd, J=6.2, 2.7 Hz), 4.93 (1H, d, J=8.7 Hz), 5.30 (1H, d, J=16.5 Hz), 5.50 (2H, s), 5.58 (1H, dd, J=10.2, 6.9 Hz), 5.67 (1H, d, J=6.9 Hz), 5.74 (1H, d, J=16.5 Hz), 5.80 (1H, dd, J=8.9, 2.4 Hz), 6.17 (1H, t, J=9.0 Hz), 6.23 (1H, s), 7.14 (1H, d, J=9.3 Hz), 7.30–7.87 (15H, m), 8.10 (2H, d, J=7.2 Hz), 8.28 (1H, d, J=8.4 Hz), 8.50 (1H, d, J=8.4 Hz), 9.32 (1H, s); ESI-MS m/z 1320 [M+Na]$^+$. Anal. (C$_{72}$H$_{74}$N$_4$O$_{18}$): Theory: C, 67.38; H, 5.81. Found C, 67.30; H, 5.79.

Conjugate 18: Yield 69.3% [starting with 27.8 mg (0.029 mmol) of 13]; pale yellow amorphous solid, $[\alpha]_D$ −41.3° (c 0.15, CHCl$_3$), $^1$H NMR (CDCl$_3$): δ 1.03 (3H, t, J=7.5 Hz), 1.15 (3H, s), 1.25 (3H, s), 1.57 (3H, s), 1.76 (3H, s), 2.10 (3H, s), 2.28 (3H, s), 3.80 (1H, d, J=6.6 Hz), 4.13 and 4.27 (each 1H, d, J=8.4 Hz), 4.79 (1H, d, J=2.7 Hz), 4.85 (1H, d, J=8.1 Hz), 5.31 (1H, d, J=16.5 Hz), 5.46 (1H, dd, J=10.2, 7.2 Hz), 5.55 (2H, s), 5.61 (1H, d, J=6.9 Hz), 5.74 (2H, m), 6.07 (1H, t, J=9.0 Hz), 6.12 (1H, s), 7.18 (1H, d, J=9.3 Hz), 7.32–7.88 (15H, m), 8.08 (2H, d, J=7.2 Hz), 8.30 (1H, d, J=8.4 Hz), 8.52 (1H, d, J=8.4 Hz), 9.30 (1H, s); ESI-MS m/z 1348 [M+Na]$^+$. Anal. (C$_{74}$H$_{78}$N$_4$O$_{18}$): Theory: C, 67.77; H, 5.99. Found C, 67.69; H, 5.98.

Conjugate 19: Yield 64.3% [starting with 28.2 mg (0.029 mmol) of 14]; pale yellow amorphous solid, $[\alpha]_D$ −8.0° (c 0.40, CHCl$_3$), $^1$H NMR (CDCl$_3$): δ 1.02 (3H, t, J=7.5 Hz), 1.19 (3H, s), 1.25 (3H, s), 1.95 (3H, s), 2.17 (3H, s), 2.40 (3H, s), 2.63 (3H, s), 4.00 (1H, d, J=6.3 Hz), 4.23 and 4.33 (each 1H, d, J=8.1 Hz), 4.82 (1H, d, J=2.7 Hz), 4.98 (1H, d, J=8.7 Hz), 5.14 (2H, brs), 5.28 (1H, d, J=16.2 Hz), 5.52 (2H, s), 5.67–5.76 (2H, m), 5.81 (1H, dd, J=8.7, 2.1 Hz), 6.19 (1H, t, J=9.0 Hz), 6.37 (1H, s), 7.21–7.96 (20H, m), 8.12 (2H, d, J=7.2 Hz), 8.27 (1H, d, J=8.4 Hz), 8.42 (1H, d, J=8.4 Hz), 9.39 (1H, s); ESI-MS m/z 1396 [M+Na]$^+$. Anal. (C$_{76}$H$_{74}$N$_4$O$_{18}$): Theory: C, 68.56; H, 5.60. Found C, 68.40; H, 5.56.

Conjugate 20: Yield 55.1% [starting with 23.3 mg (0.023 mmol) of 15]; pale yellow amorphous solid, $[\alpha]_D$ −11.5° (c 0.27, CHCl$_3$), $^1$H NMR (CDCl$_3$): δ 1.06 (3H, t, J=7.5 Hz), 1.18 (3H, s), 1.25 (3H, s), 1.84 (3H, s), 1.85 (3H, s), 2.17 (3H, s), 2.39 (3H, s), 3.94 (1H, d, J=6.6 Hz), 4.20 and 4.33 (each 1H, d, J=8.4 Hz), 4.81 (1H, brs), 4.96 (1H, d, J=9.3 Hz), 5.33 (1H, d, J=16.5 Hz), 5.58 (1H, m), 5.70 (1H, d, J=5.7 Hz), 5.73 (2H, s), 5.81 (1H, d, J=5.7 Hz), 6.19 (1H, t, J=9.0 Hz), 6.26 (1H, s), 7.08 (1H, d, J=9.3 Hz), 7.27–7.80 (18H, m), 7.88 (1H, t, J=7.2 Hz), 8.12 (2H, d, J=7.2 Hz), 8.33 (1H, d, J=8.4 Hz), 8.56 (1H, d, J=8.4 Hz), 9.55 (1H, s); ESI-MS m/z 1368 [M+Na]$^+$. Anal. (C$_{78}$H$_{78}$N$_4$O$_{18}$): Theory: C, 68.91; H. 5.78. Found C, 68.86; H, 5.77.

TABLE 1

Elemental Analysis Data for Conjugates 16–20

| Compound Formula | Calculated | | Found | |
|---|---|---|---|---|
| | C | H | C | H |
| 16  C$_{71}$H$_{72}$N$_4$O$_{18}$ | 67.18 | 5.72 | 67.12 | 5.69 |
| 17  C$_{72}$H$_{74}$N$_4$O$_{18}$ | 67.38 | 5.81 | 67.30 | 5.79 |
| 18  C$_{74}$H$_{78}$N$_4$O$_{18}$ | 67.77 | 5.99 | 67.69 | 5.98 |
| 19  C$_{76}$H$_{74}$N$_4$O$_{18}$ | 68.56 | 5.60 | 68.40 | 5.56 |
| 20  C$_{78}$H$_{78}$N$_4$O$_{18}$ | 68.91 | 5.78 | 68.86 | 5.77 |

Human Tumor Cell Replication Assay. Compounds were tested as inhibitors of cell growth against a limited panel of solid tumor lines including KB (epidermoid carcinoma, CL 17) and a camptothecin-resistant sub-line called KB-CPT; HCT-8 (ileocecal adenocarcinoma, CCL 244); MCF-7

(breast adenocarcinoma, HTB 22); PC-3 (prostate adenocarcinoma, CRL 1435); 1A9 (ovarian carcinoma) and a paclitaxel resistant sub-line called PTX10 with mutated β-tubulin. Drug-resistant cell lines were generous gifts of Dr. Y. C. Cheng (Yale University, New Haven, Conn.) and Dr. P. Giannakakou (NIH, Bethesda, Md.). Cell lines were adapted for growth in RPMI-1640 medium supplemented with 25 mM Hepes, 2% $NaHCO_3$, 10% (v/v) fetal calf serum and 100 μg/mL kanamycin. Cultures were maintained in a 5% $CO_2$ atmosphere at 37° C. The sulforhodamine B microtiter plate assay described by Rubinstein et al. (1990) *J. Natl. Cancer Inst.* 82:1113, was used to evaluate compounds as inhibitors of cell replication. The $ED_{50}$ value, the concentration of compound that inhibited cell line replication by 50% relative to control after three days of continuous exposure was interpolated from dose-response graphs fitted to data using Prizm (GraphPad software, San Diego, Calif.).

DNA Topoisomerase I Activity Assay. Compounds were tested as inhibitors of enzyme catalyzed plasmid DNA relaxation. Reactions contained 0.5 μg pBR322 DNA and 0.5 U human DNA Topoisomerase I (TopoGen, Columbus, Ohio), compounds at 50 μM and buffer components described previously in Krishnan et al. (2000) *Anticancer Drug Design* 15:255. After 15 min at 37° C., reactions were terminated by adding proteinase K (0.1 mg/mL) and 1% (w/v) SDS. After 1 hour at 50° C., DNA was resolved on a 1% (w/v) agarose gel containing 0.5 mg/mL ethidium bromide in standard TBE buffer, and photographed under UV light using polaroid 667 film.

B. Results and Discussion

The aim of this work was to investigate whether an antitumor agent displaying multiple antitumor activity or improved activity against drug resistant cells could be prepared through conjugation between paclitaxel (1) and camptothecin (2) derivatives, and how their antitumor effects are affected by the conjugation. We report herein the synthesis and evaluation of paclitaxel-camptothecin conjugates as cytotoxic agents and DNA topo I inhibitors.

The choice of the linkage position was based on the known tolerance of the C-7 ester group in the taxane nucleus (Nicolaou et al. (1994) *Angew. Chem. Intl. Ed. Engl.* 106:15, Guy et al. (1996) *Chem. Biol.* 3:1021) and recent SAR study of 7-substituted camptothecin analogues (Wang et al. (1994) *Bioorg. Med. Chem.* 2:1397, Wang et al. (1990) *J. Med. Chem.* 33:2660). However, the C-2' hydroxyl group of the paclitaxel side chain is normally the most reactive and selective C-7 acylation can be achieved only when C-2' is protected. The procedure of Nicolaou et al. (1994) *Angew. Chem. Intl. Ed. Engl.* 106:15 was used for the preparation of C-7 amino-functionalized paclitaxels (11–15). Thus, 2'-carboxybenzyl (Cbz)-paclitaxel was treated with N-Cbz-amino acids in the presence of DCC and DMAP in $CH_2Cl_2$ to give 6–10 in good yields. Subsequent reductive removal of both Cbz groups by hydrogenation gave the desired C-7 amino-functionalized paclitaxels (11–15). Five paclitaxel-camptothecin conjugates (16–20) were obtained by conjugation of 11–15 with 7-formyl-camptothecin (5) in benzene as shown in Scheme 1. Compounds 16–20 were unstable on silica gel (the parental compounds were regenerated), but could be purified by Sephadex LH-20 column chromatography. All conjugates (16–20) showed the characteristic imine proton signal at δ 9.30–0.55 in their $^1$H-NMR spectra.

The five conjugates (16–20) were tested for cytotoxicity against a panel of human tumor cell lines (HTCL) including paclitaxel-resistant and camptothecin-resistant derivatives as described in Rubinstein et al. (1990) *J. Natl. Cancer Inst.* 82:1113. The results are shown in Table 2 with the values for paclitaxel (1) and camptothecin (2) given for comparison.

TABLE 2

Activity of Paclitaxel-Camptothecin Conjugates 16–20 as Inhibitors of Cancer Cell Replication[a]

| Compound | Cell Line/$ED_{50}$ | | | | | | | |
|---|---|---|---|---|---|---|---|---|
| | KB | KB-CPT | IA9 | IA9-PTX10 | HCT8 | MCF-7 | PC-3 | Mean $ED_{50}$[b] |
| Paclitaxel | −12.1 | −12.2 | −12.2 | −11.7 | −7.1 | −13.9 | −10.3 | −11.1 |
| Camptothecin | −10.8 | −7.5 | −10.2 | −9.4 | −9.3 | −7.1 | −7.1 | −8.9 |
| 16 | <−11.0 (67) | −11.1 | <−11.0 (76) | −10.9 | −10.6 | −7.1 | −7.0 | <−9.3 |
| 17 | −10.4 | −9.7 | −10.2 | −10.5 | −10.0 | −7.1 | −7.1 | −9.0 |
| 18 | −9.3 | −8.1 | −10.0 | −10.5 | −10.6 | −7.5 | −7.5 | −9.0 |
| 19 | −8.5 | −8.9 | −8.1 | −8.4 | −8.1 | −6.0 | −7.5 | −7.6 |
| 20 | −10.8 | −8.1 | −8.3 | −7.1 | −7.4 | >−4.0 (48) | >−5.0 (45) | >−7.1 |

[a]Effects on tumor cell line replication were determined using a standard method as described in Krishnan et al. (2000) Anticancer Drug Design 15:255. Cell line/$ED_{50}$ in $log_{10}$ M (replicates varied no more than 5%). If inhibition <50% at highest test concentration or >50% at lowest, the observed percentage inhibition observed is the bracketed value.
[b]Mean value is taken from HTCL data and does not include values for drug-resistant variants.

Figure 3A:
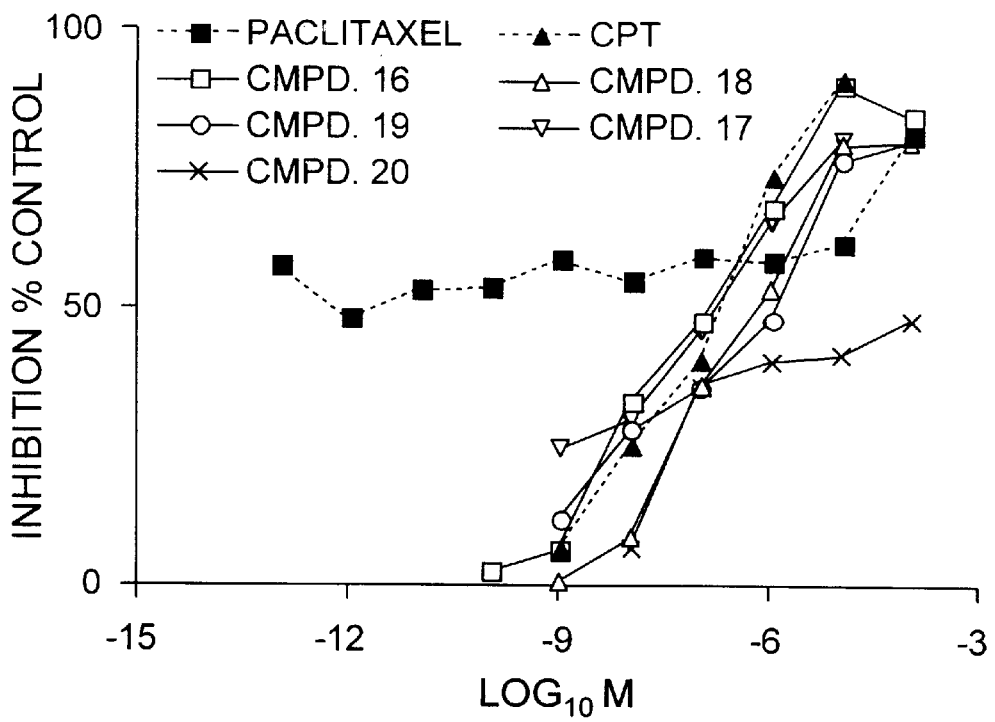
FIG. 3 illustrates the activity profiles of compounds against MCF-7 (Panel A) and HCT-8 cell replication (Panel B)
Figure 3B:
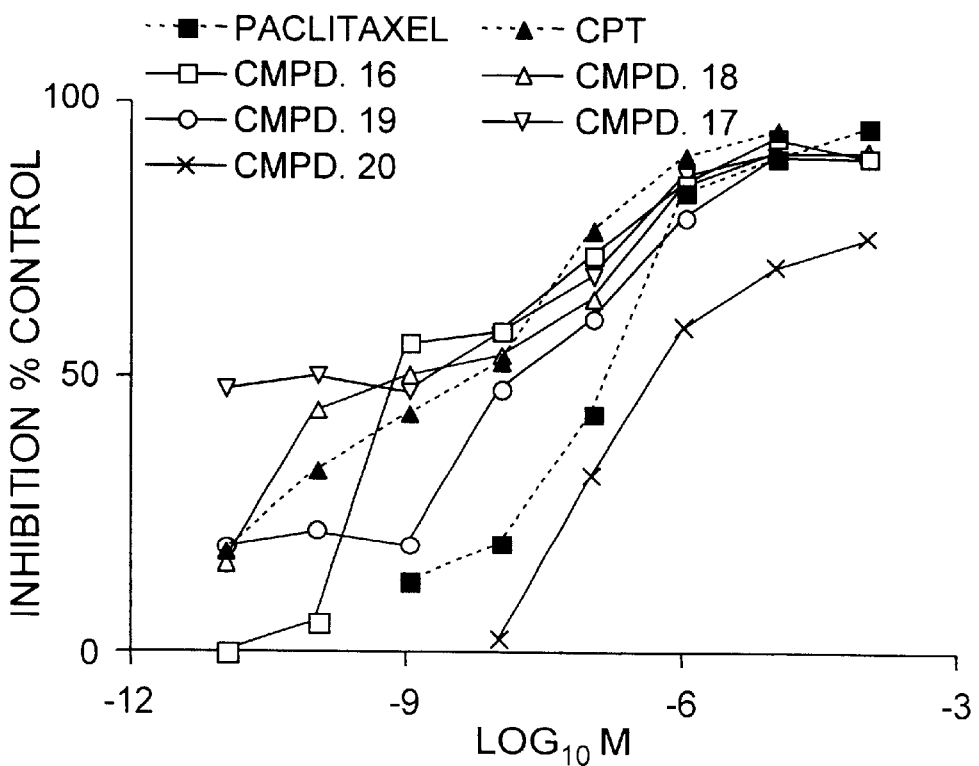

Activity profiles for the conjugates against MCF-7 (breast cancer) and HCT-8 (colon adenocarcinoma) cells are shown in FIG. 3, panel A and panel B, respectively. All of the conjugates were potent inhibitors of tumor cell replication with improved activity relative to 2(camptothecin), and also showed better activity than 2 against camptothecin-resistant KB-CPT cells. Significantly, as shown in FIG. 3, 16–18 were more active against HCT-8 cell replication than both 1(paclitaxel) and 2. Structure-Activity Relationship (SAR) consideration of the linker between the paclitaxel and camptothecin moieties showed that 16–18, in which paclitaxel and camptothecin were linked by aliphatic amino acids, showed better cytotoxic activity than 19 and 20, in which paclitaxel and camptothecin were linked by aromatic amino acids.

Figure 4:
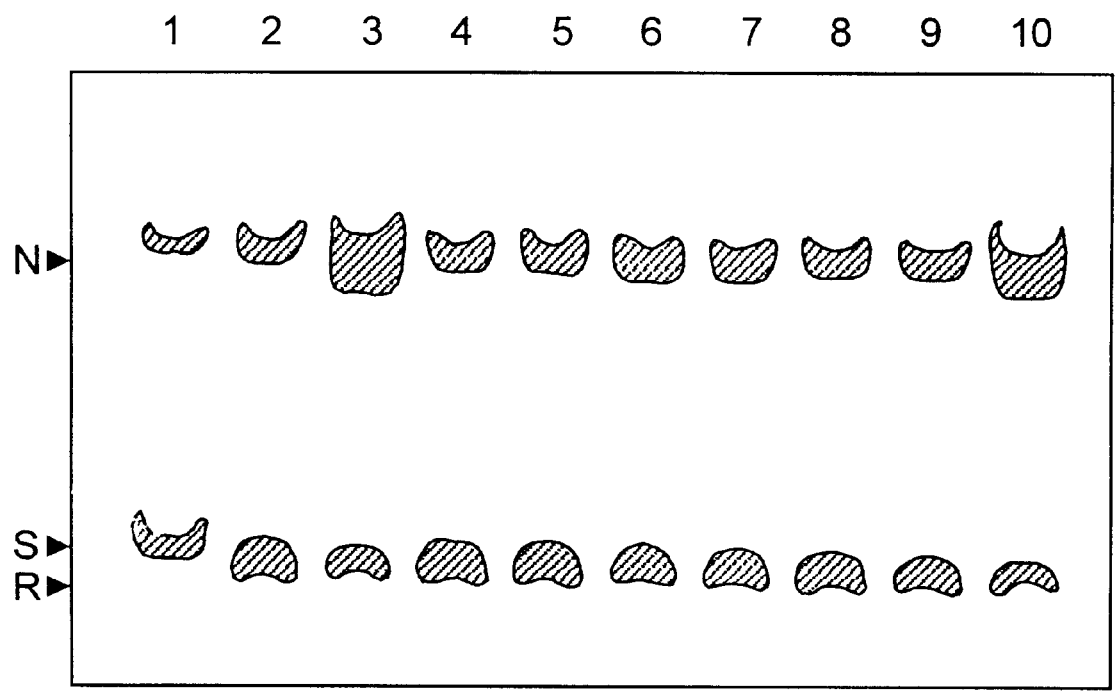
FIG. 4 illustrates an ethidium bromide-containing agarose gel displaying compounds of the present invention as human DNA topoisomerase I inhibitors.

Conjugates 16–20 were also tested as inhibitors of human DNA topo I activity in vitro (FIG. 4) in the manner as described in Krishnan et al. (2000) *Anticancer Drug Design* 15:255. All of the conjugates were significantly less potent than 2 in this assay. Compounds 16, 18, and 19 showed only marginal activity at 50 M, while 17 and 20 were inactive. None of the conjugates inhibited DNA relaxation.

Based on activity against drug-resistant cell line replication, one could conclude that the conjugates are simply acting as "weak taxanes", but the spectrum of activity, particularly against MCF-7 and HCT-8 (FIG. 3), is not consistent with this conclusion. The latter results indicate that, compared with 1 and 2, the cytotoxicity profiles of 16–18 are quite distinctive. In addition, because the results from the DNA topo I inhibition assay show that the conjugates, unlike 2, are not DNA topo I inhibitory in vitro, it is likely that a novel mechanism of action has been achieved through conjugation.

The foregoing is illustrative of the present invention, and is not to be construed as limiting thereof. The invention is defined by the following claims, with equivalents of the claims to be included therein.

What is claimed is:

1. A compound according to formula I:

C'—L—T (I)

wherein:

C' is a camptothecin group of formula II:

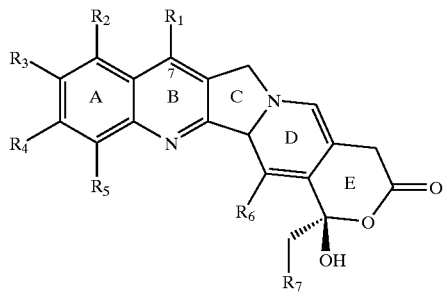

wherein:
- $R_1$ is selected from the group consisting of H, alkyl, aldehyde, carbonyl, alkoxy, alkylaryl, hydroxyalkyl, haloalkyl, aminoalkyl, dialkylamino, dialkylaminoalkyl, cycloaminoalkyl, aryl, aryloxy, C-glycal, nitro, cyano and O-glycosyl;
- $R_2$, $R_3$, $R_4$ and $R_5$ are each independently selected from the group consisting of H, amino, hydroxy, alkyl, alkoxy, alkylthiol, alkylamino, aminoalkyl, di(alkyl) amino, cycloaminoalkyl, aminoalkoxy, aryl, aryloxy, C-glycal, cyano, methylenedioxy, formyl, nitro, halo, azido, amido, hydrazino, any of the twenty standard amino acids bonded to the A ring via the amino-nitrogen atom, $SR_8$, $NR_8R_8$, or O-glycosyl; or $R_3$ and $R_4$ together form a 5- or 6-member aromatic or dioxolane ring; and wherein $R_2$ and $R_3$, $R_3$ and $R_4$, or $R_4$ and $R_5$ taken together;
- Subject to the proviso that one of $R_1$, $R_2$, $R_3$, $R_4$ and $R_5$ is a covalent bond to L;
- $R_6$ is H, halo, alkyl, alkoxy, alkylaryl, hydroxyalkyl, or haloalkyl;
- $R_7$ is alkyl, alkylaryl, hydroxyalkyl, or aryl;
- $R_8$ is independently selected from the group consisting of H, alkyl, alkylaryl, hydroxyalkyl, aminoalkyl, acyl, or aryl;

L is a linking moiety;

T is a taxoid group, of formula III:

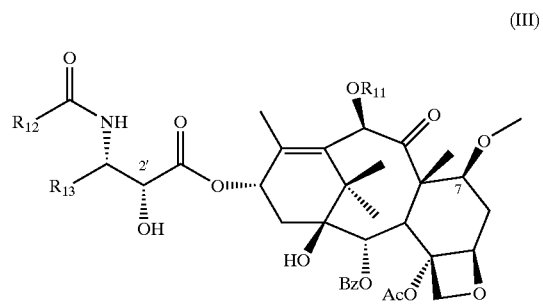

wherein:
- $R_{11}$ is selected from the group consisting of H, alkyl, alkoxy, aminoalkyl and acyl;
- $R_{12}$ and $R_{13}$ are each independently selected from the group consisting of H, alkyl, aryl, alkoxy, alkylaryl, hydroxyalkyl, haloalkyl, aminoalkyl, dialkylamino, dialkylaminoalkyl, cycloaminoalkyl, aryloxy, nitro, cyano, and halo; or a pharmaceutically acceptable salt thereof.

2. A compound according to claim 1, wherein $R_1$ is a formyl group.

3. A compound according to claim 1, wherein $R_6$ is a halogen.

4. A compound according to claim 1, wherein $R_{11}$ is an acyl group and $R_{12}$ and $R_{13}$ are each independently a phenyl group.

5. A compound according to claim 1, wherein $R_{11}$ is H, $R_{12}$ is a t-butoxy group and $R_{13}$ is a phenyl group.

6. A compound according to claim 1, wherein L is a linking moiety at position 7 of said taxoid group and at $R_1$ of said camptothecin group of the formula IV:

—X—$R_{21}$—A— (IV)

wherein:
- X is an electron withdrawing group; and
- $R_{21}$ is selected from the group consisting of alkylene and arylalkylene; and
- A is selected from the group consisting of amino and imine.

7. A compound according to claim 1, wherein said linking moiety comprises an ester and imine linkage.

8. A compound according to claim 1, wherein said linking moiety comprises the formula V:

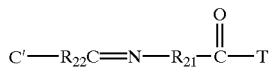

wherein:
- $R_{21}$ is selected from the group consisting of alkylene and arylalkylene; and
- $R_{22}$ is selected from the group consisting of H and alkyl.

9. A compound according to claim 1, wherein said linking moiety comprises aliphatic amino acids.

10. A compound according to claim 1, wherein said linking moiety comprises aromatic amino acids.

11. A compound according to claim 1, wherein L is a linking moiety of the formula —$L_a$—$L_b$— where $L_b$ is present or absent and $L_a$ and $L_b$ are each independently selected from the group consisting of:

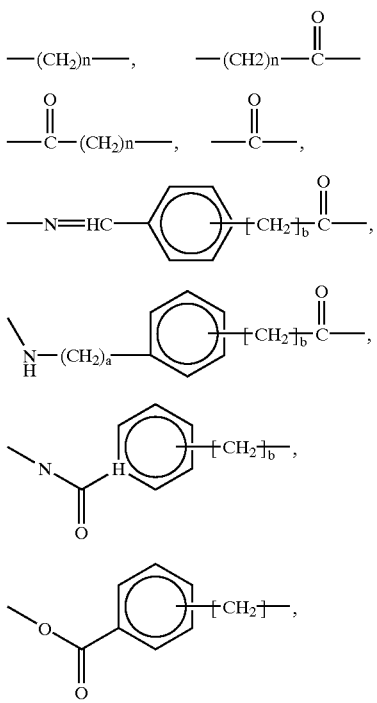
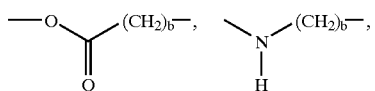
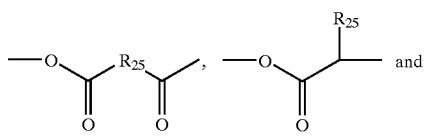
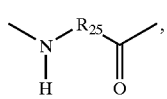
wherein:
n is 0 to 6, a is 0 to 3 and b is 0 to 3; and $R_{25}$ is selected from the group consisting of alkylene, alkenyl, and arylenyl.
12. A compound of claim 1 having the structure
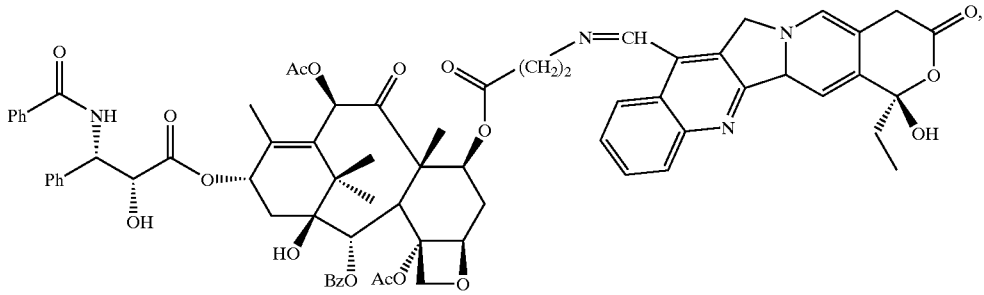
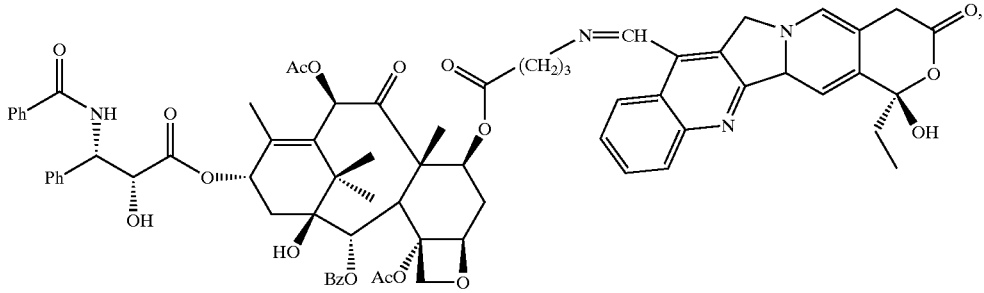
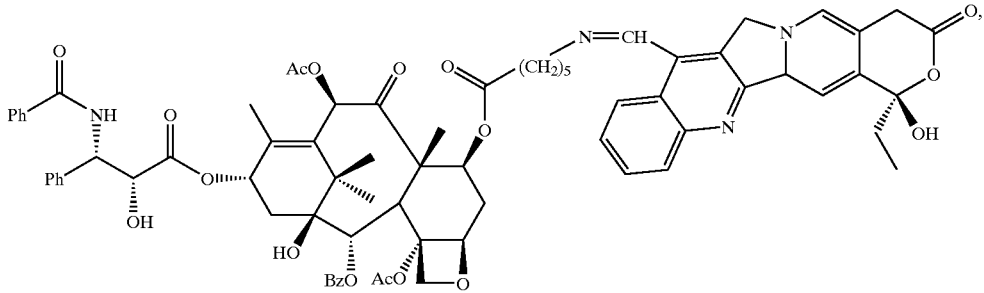

-continued

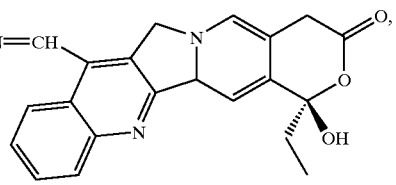
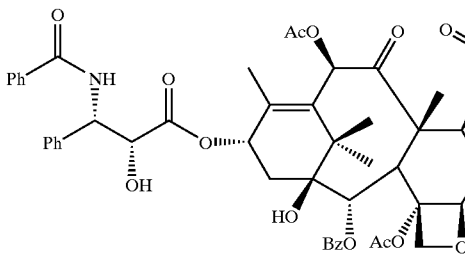

and

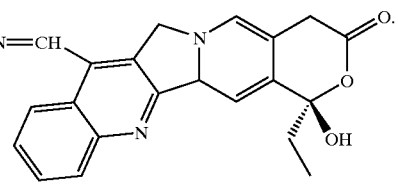
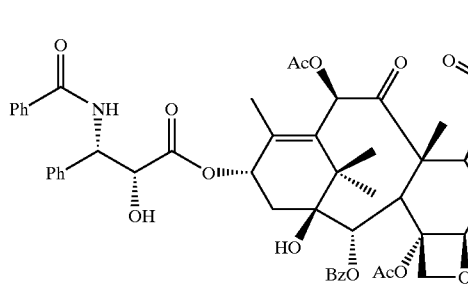

13. A pharmaceutical formulation comprising a compound according to claim 1 in a pharmaceutically acceptable carrier.

14. A pharmaceutical formulation according to claim 1, wherein said carrier is an aqueous carrier.

15. A method of treating a cancer, comprising administering to a subject in need thereof a treatment effective amount of a compound according to claim 1.

16. The method according to claim 15, wherein said cancer is selected from the group consisting of small cell lung cancer, testicular cancer, lymphoma, leukemia, esophageal cancer, stomach cancer, colon cancer, breast cancer, ovarian cancer, central nervous system cancer, liver cancer and prostate cancer.

17. The method according to claim 15, wherein said cancer is breast cancer.

18. The method according to claim 15, wherein said cancer is ovarian cancer.

19. The method according to claim 15, wherein said cancer is prostate cancer.

20. The method according to claim 15, wherein said cancer is resistant to camptothecin.

21. The method according to claim 15, wherein said cancer is resistant to paclitaxel.

22. The method according to claim 15, wherein said cancer is resistant to both camptothecin and paclitaxel.

23. A method of inducing cellular differentiation, said method comprising contacting a cancer cell with a differentiation effective amount of a compound according to claim 1.

24. A method according to claim 23, wherein said contacting step is carried out in vivo.

25. A method according to claim 23, wherein said contacting step is carried out in vitro.

26. A method of inhibiting cellular mitosis, comprising contacting a cell with a mitosis inhibiting amount of a compound according to claim 1.

27. A method according to claim 26, wherein said contacting step is carried out in vivo.

28. A method according to claim 26, wherein said contacting step is carried out in vitro.

* * * * *